United States Patent [19]

Mizumura et al.

[11] Patent Number: 5,602,014
[45] Date of Patent: Feb. 11, 1997

[54] REGULATORY SYSTEM FOR EXPRESSION OF NITRILASE GENE

[75] Inventors: Yurie Mizumura; Fujio Yu, both of Yokohama, Japan

[73] Assignee: Nitto Chemical Industry Co., Ltd., Tokyo, Japan

[21] Appl. No.: 577,184

[22] Filed: Dec. 22, 1995

[30] Foreign Application Priority Data

Dec. 28, 1994 [JP] Japan ................................. 6-337652

[51] Int. Cl.$^6$ ........................... C12N 15/00; C12N 15/09; C12N 1/21; C12P 21/00
[52] U.S. Cl. ................... 435/129; 435/69.1; 435/252.3; 435/320.1; 935/22; 935/23; 935/27; 935/33; 935/39; 935/72; 536/23.7
[58] Field of Search .................... 435/320.1, 69.1, 435/252.3, 129; 935/22, 23, 27, 33, 39, 72; 536/23.7

*Primary Examiner*—David Guzo
*Assistant Examiner*—Bonnie Weiss
*Attorney, Agent, or Firm*—Oblon, Spivak, McClelland, Maier & Neustadt, P.C.

[57] ABSTRACT

The invention relates to a regulatory factor or system composed of 2 components of a polypeptide having the amino acid sequence of SEQ ID No:1 and a polypeptide having the amino acid sequence of SEQ ID No:2 to activate a nitrilase gene promoter, as well as to DNA coding therefor. Nitrilase can be produced by introducing the gene coding for the present regulatory factor together with a nitrilase gene containing a promoter region into a microorganism of the genus Rhodococcus.

19 Claims, 2 Drawing Sheets

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
  ( A ) LENGTH: 244 amino acids
  ( B ) TYPE: amino acid
  ( C ) STRANDEDNESS:
  ( D ) TOPOLOGY: linear ( i i ) MOLECULE TYPE: protein ( v i ) ORIGINAL SOURCE:
  ( A ) ORGANISM: RHODOCOCCUS ERYTHROPOLIS
  ( B ) STRAIN: SK92

( x i ) SEQUENCE DESCRIPTION: SEQ ID NO:1:

```
Met Ala Gly Ala Asp Val His Ala Gln Gly Gly Thr Asn Arg Arg Ala
 1               5                  10                  15

Arg Ile Leu Val Val Asp Asp Glu Lys His Val Arg Thr Met Val Thr
                20                  25                  30

Trp Gln Leu Glu Ser Glu Asn Phe Asp Val Val Ala Ala Ala Asp Gly
                35                  40                  45

Asp Ala Ala Leu Arg Gln Val Thr Glu Ser Ala Pro Asp Leu Met Val
        50                  55                  60

Leu Asp Leu Ser Leu Pro Gly Lys Gly Gly Leu Glu Val Leu Ala Thr
 65                  70                  75                  80

Val Arg Arg Thr Asp Ala Leu Pro Ile Val Val Leu Thr Ala Arg Arg
                     85                  90                  95

Asp Glu Thr Glu Arg Ile Val Ala Leu Asp Leu Gly Ala Asp Asp Tyr
                100                 105                 110

Val Ile Lys Pro Phe Ser Pro Arg Glu Leu Ala Ala Arg Ile Arg Ala
            115                 120                 125

Val Leu Arg Arg Thr Thr Ala Glu Pro Pro His Glu Ala Ala Val Gln
        130                 135                 140

Arg Phe Gly Asp Leu Glu Ile Asp Thr Ala Ala Arg Glu Val Arg Leu
145                 150                 155                 160

His Gly Ile Pro Leu Glu Phe Thr Thr Lys Glu Phe Asp Leu Leu Ala
                    165                 170                 175

Tyr Met Ala Ala Ser Pro Met Gln Val Phe Ser Arg Arg Arg Leu Leu
                180                 185                 190

Leu Glu Val Trp Arg Ser Ser Pro Asp Trp Gln Gln Asp Ala Thr Val
            195                 200                 205

Thr Glu His Val His Arg Ile Arg Arg Lys Ile Glu Glu Asp Pro Thr
        210                 215                 220

Lys Pro Thr Ile Leu Gln Thr Val Arg Gly Ala Gly Tyr Arg Phe Asp
225                 230                 235                 240

Gly Glu Arg Ala
```

( 2 ) INFORMATION FOR SEQ ID NO:2:

( i ) SEQUENCE CHARACTERISTICS:
  ( A ) LENGTH: 534 amino acids
  ( B ) TYPE: amino acid
  ( C ) STRANDEDNESS:
  ( D ) TOPOLOGY: linear (ii) MOLECULE TYPE: protein (vi) ORIGINAL SOURCE:
    (A) ORGANISM: RHODOCOCCUS ERYTHROPOLIS
    (B) STRAIN: SK92

(xi) SEQUENCE DESCRIPTION: SEQ ID NO:2:

```
Met Met Thr Asp Thr Leu Pro Ser Ser Ser Arg Trp Thr Leu Glu Gly
 1               5                  10                  15

Pro His Leu Gln Pro Leu Gln Gly Glu Ala Leu Ala Asp Leu His Ala
                20                  25                  30

Arg Thr Leu Glu Met Ile Thr Ser Gly Arg Glu Leu His Glu Thr Leu
            35                  40                  45

Glu Val Val Ala Arg Gly Ile Glu Glu Leu Met Pro Gly Lys Arg Cys
        50                  55                  60

Ala Ile Leu Leu Leu Asp Asn Thr Gly Pro Val Leu Arg Cys Gly Ala
65                  70                  75                  80

Ala Pro Thr Met Ser Ala Pro Trp Arg Arg Trp Ile Asp Ser Leu Val
                85                  90                  95

Pro Gly Pro Met Ser Gly Gly Cys Gly Thr Ala Val His Leu Gly Glu
               100                 105                 110

Pro Val Ile Ser Tyr Asp Val Ala Asp Asp Pro Lys Phe Arg Gly Pro
           115                 120                 125

Phe Arg Ala Ala Ala Leu His Glu Gly Ile Arg Ala Cys Trp Ser Thr
    130                 135                 140

Pro Val Thr Ser Gly Asp Gly Thr Ile Leu Gly Thr Phe Ala Ile Tyr
145                 150                 155                 160

Gly Ser Val Pro Ala Phe Pro Ala Gln Gln Asp Val Ala Leu Val Thr
                165                 170                 175

Gln Cys Thr Asp Leu Thr Ala Ala Val Ile Thr Thr His Lys Leu His
            180                 185                 190

Gln Asp Leu Ser Met Ser Glu Glu Arg Phe Arg Arg Ala Phe Asp Ser
        195                 200                 205

Asn Val Val Gly Met Ala Leu Leu Asp Glu Ser Gly Ser Ser Ile Arg
    210                 215                 220

Val Asn Asp Thr Leu Cys Ala Leu Thr Ala Ala Pro Pro Arg Arg Leu
225                 230                 235                 240

Leu Gly His Pro Met Gln Glu Ile Leu Thr Ala Asp Ser Arg Glu Pro
                245                 250                 255

Phe Ala Asn Gln Leu Ser Ser Ile Arg Glu Gly Leu Thr Asp Gly Gly
            260                 265                 270

Gln Leu Asp Gly Arg Ile Gln Thr Thr Gly Gly Arg Trp Ile Pro Val
        275                 280                 285

His Leu Ser Ile Ser Gly Met Trp Thr Thr Glu Arg Glu Phe Met Gly
    290                 295                 300

Phe Ser Val His Val Leu Asp Ile Ser Glu Arg Leu Ala Ala Glu Arg
305                 310                 315                 320

Ala Arg Glu Glu Gln Leu Glu Ala Glu Val Ala Arg His Thr Ala Glu
                325                 330                 335

Glu Ala Ser Arg Ala Lys Ser Thr Phe Leu Ser Gly Met Thr His Glu
            340                 345                 350

Val Gln Thr Pro Met Ala Val Ile Val Gly Phe Ser Glu Leu Leu Glu
        355                 360                 365

Thr Leu Asp Leu Asp Glu Glu Arg Arg Gln Cys Ala Tyr Arg Lys Ile
    370                 375                 380
```

| | | | | | | | | | | | | | | | |
|---|---|---|---|---|---|---|---|---|---|---|---|---|---|---|---|
| Gly | Glu | Ala | Ala | Lys | His | Val | Ile | Ser | Leu | Val | Asp | Asp | Val | Leu | Asp |
| 385 | | | | | 390 | | | | | 395 | | | | | 400 |
| Ile | Ala | Lys | Ile | Glu | Ala | Gly | Ala | Ile | Thr | Leu | Gln | Asp | Glu | Asp | Ile |
| | | | | 405 | | | | | 410 | | | | | 415 | |
| Asp | Leu | Ser | Glu | Glu | Val | Ala | Thr | Ile | Val | Glu | Met | Leu | Glu | Pro | Ile |
| | | | 420 | | | | | 425 | | | | | 430 | | |
| Ala | Arg | Asp | Arg | Asp | Arg | Asp | Val | Cys | Leu | Arg | Tyr | Val | Pro | Pro | Gln |
| | | 435 | | | | | 440 | | | | | 445 | | | |
| Thr | Pro | Val | His | Val | Cys | Ser | Asp | Arg | Arg | Arg | Val | Arg | Glu | Val | Leu |
| | 450 | | | | | 455 | | | | | 460 | | | | |
| Leu | Asn | Ile | Val | Ser | Asn | Gly | Ile | Lys | Tyr | Asn | Arg | Leu | Gly | Gly | Val |
| 465 | | | | | 470 | | | | | 475 | | | | | 480 |
| Val | Asp | Pro | Pro | Thr | Gly | Ser | Gly | Ala | Ala | Arg | Pro | Arg | Gln | Thr | Arg |
| | | | | 485 | | | | | 490 | | | | | 495 | |
| Ala | Pro | Asp | Tyr | Pro | Ala | Thr | Pro | Thr | Thr | Asn | Ser | Ser | Ser | Pro | Ser |
| | | | 500 | | | | | 505 | | | | | 510 | | |
| Thr | Gly | Trp | Glu | Ser | Arg | Pro | Arg | Gly | Cys | Lys | Gly | Arg | Gly | Ser | Val |
| | | | 515 | | | | 520 | | | | | 525 | | | |
| Leu | Arg | Ser | Pro | Ala | Arg | | | | | | | | | | |
| | 530 | | | | | | | | | | | | | | |

( 2 ) INFORMATION FOR SEQ ID NO:3:

( i ) SEQUENCE CHARACTERISTICS:
        ( A ) LENGTH: 735 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: RHODOCOCCUS ERYTHROPOLIS
        ( B ) STRAIN: SK92

( x i ) SEQUENCE DESCRIPTION: SEQ ID NO:3:

| | | | | | |
|---|---|---|---|---|---|
| ATGGCCGGAG | CGGACGTCCA | CGCCCAGGGT | GGCACGAATC | GACGTGCACG | CATCCTCGTC | 60 |
| GTCGACGACG | AAAACACGT | GCGCACGATG | GTGACGTGGC | AACTCGAATC | GGAGAATTTC | 120 |
| GATGTTGTCG | CTGCGGCAGA | CGGAGATGCG | GCACTGCGTC | AGGTCACTGA | GAGCGCACCC | 180 |
| GATTTGATGG | TGCTCGATCT | GTCGCTCCCG | GGGAAAGGTG | GGTTGGAAGT | GCTCGCTACG | 240 |
| GTCCGCAGAA | CCGATGCACT | GCCTATCGTC | GTGCTCACAG | CACGCCGCGA | TGAAACCGAA | 300 |
| CGGATCGTCG | CGCTGGATCT | CGGCGCCGAT | GACTACGTCA | TCAAACCGTT | CTCCCCGCGG | 360 |
| GAATTGGCCG | CCCGTATCCG | GGCAGTGCTT | CGTCGAACCA | CAGCTGAACC | CCACACGAG | 420 |
| GCGGCGGTTC | AGCGATTCGG | TGACCTAGAG | ATCGACACCG | CTGCGCGCGA | GGTTCGGCTC | 480 |
| CACGGGATAC | CGCTCGAGTT | CACCACCAAG | GAGTTCGATC | TGCTGGCCTA | TATGGCCGCA | 540 |
| TCACCGATGC | AGGTCTTCAG | CCGACGCAGA | TTGTTGCTCG | AGGTGTGGCG | ATCGTCGCCC | 600 |
| GACTGGCAGC | AGGACGCCAC | CGTGACCGAG | CACGTGCACC | GCATTCGCCG | CAAGATCGAA | 660 |
| GAAGATCCCA | CCAAACCGAC | GATCCTGCAG | ACAGTGCGGG | GAGCCGGTTA | CCGTTTCGAC | 720 |
| GGAGAGCGTG | CATGA | | | | | 735 |

( 2 ) INFORMATION FOR SEQ ID NO:4:

( i ) SEQUENCE CHARACTERISTICS:
        ( A ) LENGTH: 1605 base pairs
        ( B ) TYPE: nucleic acid
        ( C ) STRANDEDNESS: double ( D ) TOPOLOGY: linear ( i i ) MOLECULE TYPE: DNA (genomic)

( v i ) ORIGINAL SOURCE:
    ( A ) ORGANISM: RHODOCOCCUS ERYTHROPOLIS
    ( B ) STRAIN: SK92

( x i ) SEQUENCE DESCRIPTION: SEQ ID NO:4:

| | | | | | | |
|---|---|---|---|---|---|---|
| ATGATGACCG | ACACACTGCC | CTCCTCGTCC | CGTTGGACCC | TTGAAGGCCC | GCATCTCCAG | 60 |
| CCGCTGCAGG | GTGAGGCCCT | GGCGGATCTC | CACGCCCGTA | CGCTCGAGAT | GATCACTTCC | 120 |
| GGGAGAGAAT | TGCACGAGAC | ACTCGAGGTG | GTCGCCCGCG | GCATCGAGGA | ACTGATGCCG | 180 |
| GGCAAACGTT | GCGCAATTCT | GTTGCTCGAC | AACACCGGAC | CGGTATTGCG | CTGCGGCGCG | 240 |
| GCCCCAACAA | TGAGCGCGCC | GTGGCGCCGG | TGGATCGACA | GCCTCGTCCC | TGGTCCGATG | 300 |
| TCGGGTGGCT | GCGGCACAGC | GGTTCACCTC | GGCGAGCCGG | TTATTTCCTA | TGACGTGGCC | 360 |
| GATGACCCGA | AATTCCGCGG | CCCCTTCCGC | GCCGCAGCCC | TCCACGAGGG | CATACGTGCC | 420 |
| TGCTGGTCCA | CCCCCGTCAC | AAGCGGAGAC | GGCACGATCC | TCGGCACTTT | CGCGATCTAC | 480 |
| GGATCCGTGC | CGGCGTTCCC | CGCACAACAG | GACGTTGCCC | TGGTCACCCA | ATGCACCGAC | 540 |
| CTGACCGCTG | CCGTCATCAC | CACCCACAAA | CTTCATCAAG | ATCTGAGCAT | GAGCGAGGAG | 600 |
| CGGTTCCGAC | GCGCCTTCGA | TTCCAATGTC | GTCGGCATGG | CACTTCTCGA | CGAATCCGGC | 660 |
| TCCAGCATCC | GCGTCAACGA | CACCCTGTGC | GCGTTGACCG | CAGCTCCGCC | ACGGCGCCTC | 720 |
| CTCGGCCACC | CCATGCAGGA | GATACTCACC | GCCGACTCCC | GGGAACCGTT | CGCCAATCAG | 780 |
| TTGTCCTCCA | TCCGTGAGGG | ATTGACCGAC | GGCGGACAGC | TCGACGGACG | AATCCAAACC | 840 |
| ACCGGAGGTC | GGTGGATTCC | GGTGCACCTG | TCCATCAGCG | GTATGTGGAC | CACGGAGCGG | 900 |
| GAGTTCATGG | GATTCAGCGT | CCATGTCCTG | GACATCTCCG | AGCGCCTGGC | CGCCGAACGC | 960 |
| GCCCGCGAGG | AACAACTCGA | GGCCGAGGTT | GCCCGCCATA | CCGCGGAGGA | AGCCAGTCGC | 1020 |
| GCCAAGTCCA | CGTTCCTGTC | CGGCATGACG | CACGAGGTCC | AAACGCCCAT | GGCCGTTATC | 1080 |
| GTCGGATTCA | GTGAGCTACT | CGAGACGCTG | GACCTGGATG | AAGAACGTCG | TCAGTGCGCC | 1140 |
| TACCGCAAGA | TCGGCGAAGC | CGCGAAACAC | GTGATCTCCC | TGGTCGACGA | CGTTCTCGAT | 1200 |
| ATAGCCAAGA | TCGAAGCCGG | CGCTATCACT | CTGCAGGACG | AAGACATCGA | CCTGTCCGAA | 1260 |
| GAAGTTGCCA | CCATCGTGGA | GATGCTCGAG | CCCATCGCCC | GTGACCGTGA | CCGTGACGTC | 1320 |
| TGCCTGCGGT | ACGTCCCGCC | GCAGACACCG | GTGCACGTGT | GCTCGGACCG | GCGGCGGGTG | 1380 |
| CGGGAAGTGC | TGCTCAACAT | CGTCTCCAAC | GGGATCAAGT | ACAATCGGCT | CGGTGGTGTC | 1440 |
| GTCGACCCCC | CAACAGGATC | AGGGGCTGCT | CGTCCGCGTC | AGACGAGGGC | CCCGGACTAC | 1500 |
| CCAGCGACGC | CGACGACGAA | CTCTTCGAGC | CCTTCAACCG | GCTGGGAGTC | GAGGCCACGG | 1560 |
| GGGTGCAAGG | GTCGGGGCTC | GGTCTTGCGC | TCTCCCGCGC | GCTGA | | 1605 |

( 2 ) INFORMATION FOR SEQ ID NO:5:

( i ) SEQUENCE CHARACTERISTICS:
        ( A ) LENGTH: 2336 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: RHODOCOCCUS ERYTHROPOLIS
        ( B ) STRAIN: SK92

( x i ) SEQUENCE DESCRIPTION: SEQ ID NO:5:

```
ATGGCCGGAG CGGACGTCCA CGCCCAGGGT GGCACGAATC GACGTGCACG CATCCTCGTC    60
GTCGACGACG AAAAACACGT GCGCACGATG GTGACGTGGC AACTCGAATC GGAGAATTTC   120
GATGTTGTCG CTGCGGCAGA CGGAGATGCG GCACTGCGTC AGGTCACTGA GAGCGCACCC   180
GATTTGATGG TGCTCGATCT GTCGCTCCCG GGGAAAGGTG GGTTGGAAGT GCTCGCTACG   240
GTCCGCAGAA CCGATGCACT GCCTATCGTC GTGCTCACAG CACGCCGCGA TGAAACCGAA   300
CGGATCGTCG CGCTGGATCT CGGCGCCGAT GACTACGTCA TCAAACCGTT CTCCCCGCGG   360
GAATTGGCCG CCCGTATCCG GGCAGTGCTT CGTCGAACCA CAGCTGAACC CCCACACGAG   420
GCGGCGGTTC AGCGATTCGG TGACCTAGAG ATCGACACCG CTGCGCGCGA GGTTCGGCTC   480
CACGGGATAC CGCTCGAGTT CACCACCAAG GAGTTCGATC TGCTGGCCTA TATGGCCGCA   540
TCACCGATGC AGGTCTTCAG CCGACGCAGA TTGTTGCTCG AGGTGTGGCG ATCGTCGCCC   600
GACTGGCAGC AGGACGCCAC CGTGACCGAG CACGTGCACC GCATTCGCCG CAAGATCGAA   660
GAAGATCCCA CCAAACCGAC GATCCTGCAG ACAGTGCGGG GAGCCGGTTA CCGTTTCGAC   720
GGAGAGCGTG CATGATGACC GACACACTGC CCTCCTCGTC CCGTTGGACC CTTGAAGGCC   780
CGCATCTCCA GCCGCTGCAG GGTGAGGCCC TGGCGGATCT CCACGCCCGT ACGCTCGAGA   840
TGATCACTTC CGGGAGAGAA TTGCACGAGA CACTCGAGGT GGTCGCCCGC GGCATCGAGG   900
AACTGATGCC GGGCAAACGT TGCGCAATTC TGTTGCTCGA CAACACCGGA CCGGTATTGC   960
GCTGCGGCGC GGCCCCAACA ATGAGCGCGC CGTGGCGCCG GTGGATCGAC AGCCTCGTCC  1020
CTGGTCCGAT GTCGGGTGGC TGCGGCACAG CGGTTCACCT CGGCGAGCCG GTTATTTCCT  1080
ATGACGTGGC CGATGACCCG AAATTCCGCG GCCCCTTCCG CGCCGCAGCC CTCCACGAGG  1140
GCATACGTGC CTGCTGGTCC ACCCCCGTCA CAAGCGGAGA CGGCACGATC CTCGGCACTT  1200
TCGCGATCTA CGGATCCGTG CCGGCGTTCC CCGCACAACA GGACGTTGCC CTGGTCACCC  1260
AATGCACCGA CCTGACCGCT GCCGTCATCA CCACCCACAA ACTTCATCAA GATCTGAGCA  1320
TGAGCGAGGA GCGGTTCCGA CGCGCCTTCG ATTCCAATGT CGTCGGCATG GCACTTCTCG  1380
ACGAATCCGG CTCCAGCATC CGCGTCAACG ACACCCTGTG CGCGTTGACC GCAGCTCCGC  1440
CACGGCGCCT CCTCGGCCAC CCCATGCAGG AGATACTCAC CGCCGACTCC CGGGAACCGT  1500
TCGCCAATCA GTTGTCCTCC ATCCGTGAGG GATTGACCGA CGGCGGACAG CTCGACGGAC  1560
GAATCCAAAC CACCGGAGGT CGGTGGATTC CGGTGCACCT GTCCATCAGC GGTATGTGGA  1620
CCACGGAGCG GGAGTTCATG GGATTCAGCG TCCATGTCCT GGACATCTCC GAGCGCCTGG  1680
CCGCCGAACG CGCCCGCGAG GAACAACTCG AGGCCGAGGT TGCCCGCCAT ACCGCGGAGG  1740
AAGCCAGTCG CGCCAAGTCC ACGTTCCTGT CCGGCATGAC GCACGAGGTC CAAACGCCCA  1800
TGGCCGTTAT CGTCGGATTC AGTGAGCTAC TCGAGACGCT GGACCTGGAT GAAGAACGTC  1860
GTCAGTGCGC CTACCGCAAG ATCGGCGAAG CCGCGAAACA CGTGATCTCC CTGGTCGACG  1920
ACGTTCTCGA TATAGCCAAG ATCGAAGCCG GCGCTATCAC TCTGCAGGAC GAAGACATCG  1980
ACCTGTCCGA AGAAGTTGCC ACCATCGTGG AGATGCTCGA GCCCATCGCC CGTGACCGTG  2040
ACCGTGACGT CTGCCTGCGG TACGTCCCGC CGCAGACACC GGTGCACGTG TGCTCGGACC  2100
GGCGGCGGGT GCGGGAAGTG CTGCTCAACA TCGTCTCCAA CGGGATCAAG TACAATCGGC  2160
TCGGTGGTGT CGTCGACCCC CCAACAGGAT CAGGGGCTGC TCGTCCGCGT CAGACGAGGG  2220
CCCCGGACTA CCCAGCGACG CCGACGACGA ACTCTTCGAG CCCTTCAACC GGCTGGGAGT  2280
CGAGGCCACG GGGGTGCAAG GGTCGGGGCT CGGTCTTGCG CTCTCCCGCG CGCTGA      2336
```

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:6:

```
AACTGCTGGG ARCACTTCCA                                            20
```

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:7:

```
GARTARTGRC CSACNGGRTC                                            20
```

REGULATORY SYSTEM FOR EXPRESSION OF NITRILASE GENE

FIELD OF THE INVENTION

The present invention relates to a regulatory factor involved in expression of a nitrilase gene and a DNA coding for the same and particularly to a regulatory factor derived from the strain *Rhodococcus erythropolis* SK92 and activating a nitrilase gene promoter, as well as to DNAs coding for the same, a recombinant plasmid containing the DNAs and a transformant transformed with said recombinant plasmid.

BACKGROUND OF THE INVENTION

As known processes of producing organic acids by conversion from their corresponding nitriles, mention may be made of chemical synthetic means and biological means. The latter involves the use of a microorganism or a microorganism-derived enzyme as a catalyst to hydrolyze nitriles, so this means is advantageous in that organic acids can be produced under mild conditions. Microorganisms belonging to the genus Rhodococcus are known as such catalysts for use in production of amides or organic acids by hydration or hydrolysis of their corresponding nitriles (see Japanese Laid-Open Patent Publication Nos. 251,192/1991, 91,189/1987, 470/1990, and 84,198/1990).

As compared with the above-mentioned conventional processes, the use of a nitrilase gene cloned for hydrolysis of nitriles by genetic recombination is expected to drastically improve the catalytic ability of the microorganism to hydrate nitriles because the microorganism can be engineered to contain multiple copies of the same gene. To obtain such a catalyst organism with higher catalytic activity, the present inventors successfully cloned a nitrilase gene from the strain *Rhodococcus erythropolis* SK92 and constructed a plasmid by inserting said gene into a region downstream of an *E. coli* lactose promoter. By introducing this plasmid into *E. coli*, the organism came to exhibit higher nitrilase activity during incubation in the presence of IPTG isopropyl-β-D-thiogalactoside). The present inventors further attempted to obtain a transformant of the genus Rhodococcus to attain higher performance as a catalyst organism. In this attempt, the nitrilase gene was inserted into a *Rhodococcus-E. coli* hybrid plasmid vector (see Japanese Laid-Open Patent Publication Nos. 4,589/1993 and 68,566/1993), and the vector thus constructed was introduced into a microorganism of the genus Rhodococcus. However, no nitrilase activity was expressed, and there is demand for a method of permitting the expression of nitrilase activity in a transformant of the genus Rhodococcus.

SUMMARY OF THE INVENTION

The present inventors speculated that the gene derived from the genus Rhodococcus is not expressed because the promoter for the nitrilase gene fails to function, and that a gene coding for a regulatory factor that allows the promoter to function might be present somewhere on the chromosomal DNA derived from SK92. Through screening, the present inventors found it in a region upstream of the nitrilase structural gene and succeeded thereby in expression of nitrilase activity in a transformant of the genus Rhodococcus.

That is, the present invention relates to a regulatory factor or system consisting of 2 components i.e. a polypeptide having the amino acid sequence of SEQ ID No:1 and a polypeptide having the amino acid sequence of SEQ ID No:2 to activate the nitrilase gene promoter, as well as to DNAs coding for them.

Introduction of the gene or genes coding for the regulatory factor of the invention along with the nitrilase gene containing its promoter permits microorganism of the genus Rhodococcus to produce nitrilase.

DETAILED DESCRIPTION OF THE INVENTION

Figure 1:
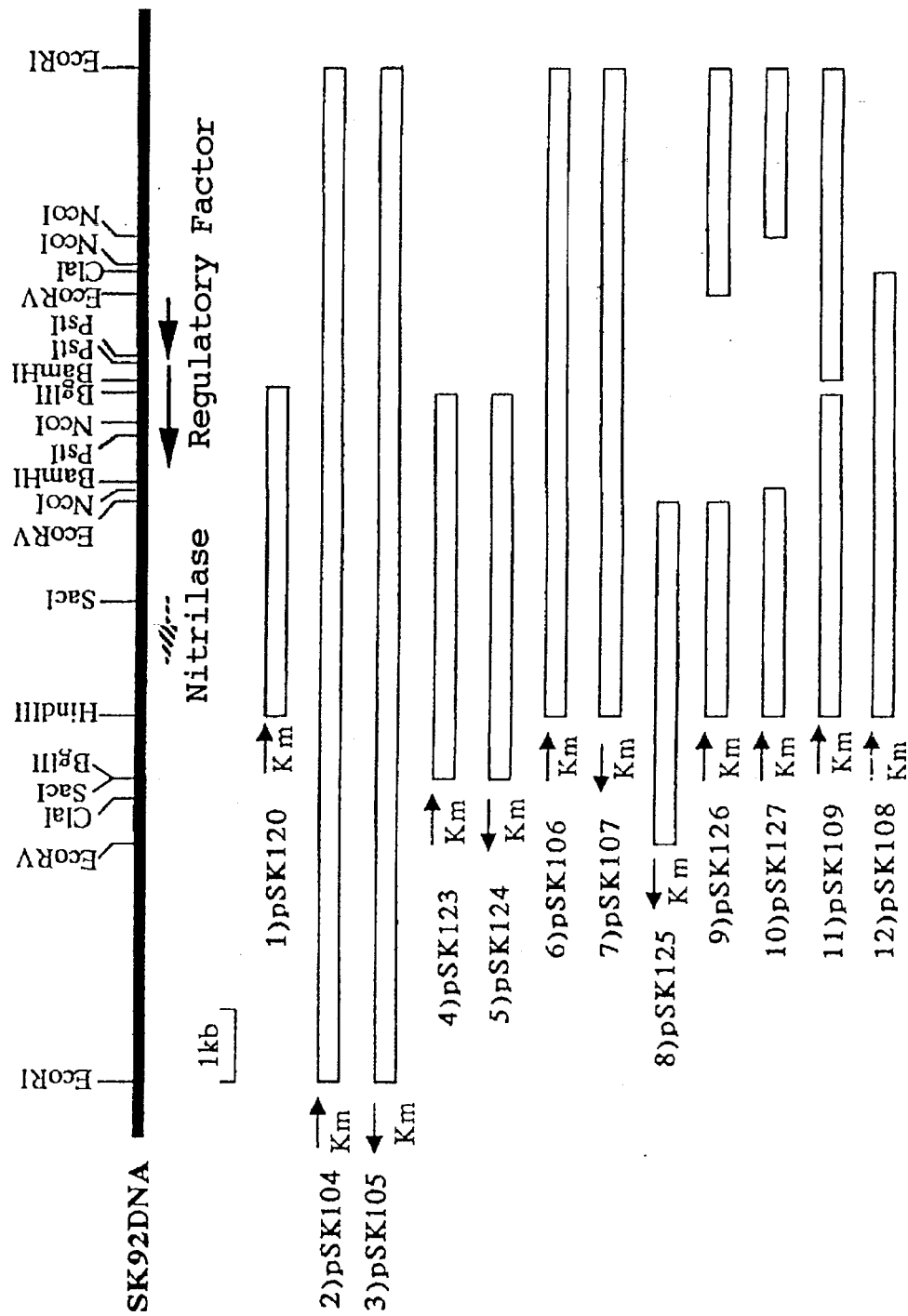
FIG. 1 shows a schematic drawing of deletion plasmids, where the arrows on the DNA fragment from SK92 indicate the location and direction of the gene coding for the regulatory factor of the invention and the gene coding for nitrilase, respectively.

Hereinafter, the present invention is described in detail. The present invention is practiced in the following steps.
(1) Preparation of Chromosomal DNA from the Strain SK92:

Chromosomal DNA is isolated from *Rhodococcus erythropolis* SK92.
(2) Construction of a DNA Library:

The chromosomal DNA is cleaved with restriction enzymes, and a DNA fragment containing the target gene is detected by Southern hybridization using the nitrilase gene of SK92 as probe. This fragment is inserted into a hybrid plasmid vector capable of replicating in cells of *E. coli* and the genus Rhodococcus to prepare a library. (3) Transformation of *E. coli* and selection of recombinant DNA:

The recombinant library constructed in step (2) is used to prepare transformants. They are subjected to colony hybridization using the probe obtained in step (2) to select a colony carrying the target recombinant DNA.
(4) Preparation of Recombinant Plasmid:

A plasmid is prepared from the recombinant obtained in step (3). (5) Transformation of a microorganism of the genus Rhodococcus and the nitrilase activity of the transformant:

The resulting plasmid is introduced into a microorganism of the genus Rhodococcus, and its nitrilase activity is determined.
(6) Deletion Plasmids and Nitrilase Activity:

Deletion plasmids are prepared by deleting various regions from the plasmid obtained in step (4) to identify the region essential for expression of the nitrilase structural gene. The plasmids prepared are not necessary to be capable of replicating in *E. coli* and are sufficient if they include a DNA region capable of replicating in cells of the genus Rhodococcus.
(7) Nucleotide Sequencing:

The nucleotide sequence of the region identified in step (6) is determined.

As the above hybrid plasmid vector, mention may be made of pK1, pK2, pK3 and pK4. These plasmids were introduced into *R. rhodochrous* ATCC 12674 and have been deposited respectively as *R. rhodochrous* ATCC 12674/pK1 (FERM BP-3728), *R. rhodochrous* ATCC 12674/pK2 (FERM BP-3729), *R. rhodochrous* ATCC 12674/pK3 (FERM BP-3730) and *R. rhodochrous* ATCC 12674/pK4 (FERM BP-3731) with the National Institute of Bioscience and Human-Technology, Agency of Industrial Science and Technology, Japan (see Japanese Laid-Open Patent Publication No. 68,556/1993).

As the above DNA region capable of replicating in cells of the genus Rhodococcus, mention may be made of those derived from plasmids pRC001, pRC002, pRC003 and pRC004, and these may be the whole of the plasmid or a partial fragment thereof. The above plasmids are derived respectively from the strains R. rhodochrous ATCC 4276, ATCC 14349, ATCC 14348 and IFO 3338 (see Japanese Laid-Open Patent Publication No. 38,556/1993).

*Rhodococcus erythropolis* SK92 has been deposited as FERM BP-3324, and the plasmid pSK108 containing the nitrilase gene and the regulatory gene has been deposited as transformant JM109/pSK108 (FERM BP-5322) carrying said plasmid pSK108, with the National Institute of Bioscience and Human-Technology, Agency of Industrial Science and Technology. The strain SK92 was previously identified as belonging to the genus Rhodococcus on the basis of its bacterial properties (see Japanese Laid-Open Patent Publication No. 280,889/1991). This organism is further identified as *Rhodococcus erythropolis* on the basis of the following detailed properties:

| ITEMS EXAMINED | RESULTS |
| --- | --- |
| decomposition of adenine | + |
| decomposition of tyrosine | + |
| decomposition of urea | + |
| utilization | |
| inositol | + |
| maltose | − |
| mannitol | + |
| rhamnose | − |
| sorbitol | + |
| sodium m-hydroxy-benzoate | − |
| sodium benzoate | + |
| sodium citrate | + |
| sodium lactate | + |
| testosterone | + |
| acetamide | + |
| sodium pyruvate | + |
| growth in the presence of 0.02% sodium azide | + |
| growth at 10° C. | + |
| growth at 40° C. | − |
| growth in the presence of 0.001% crystal violet | − |
| growth in the presence of 0.3% phenyl ethanol | − |
| growth in the presence of 5% NaCl | + |
| growth in the presence of 7% NaCl | + |

EXAMPLES

Hereinafter, the present invention will be illustrated in detail by reference to the following examples which however are not intended to limit the scope of the invention.

Cloning of the nitrilase gene from SK92 and the expression thereof in *E. coli* and Rhodococcus will be further illustrated in Reference Example.

(1) Preparation of Chromosomal DNA from SK92

The strain SK92 was incubated at 30° C. for 72 hours under shaking in 100 ml MY medium (0.5% polypeptone, 0.3% Bacto-yeast extract, 0.3% Bacto-molt extract). The cells were harvested and the pellet was suspended in 4 ml Saline-EDTA solution (0.1M EDTA, 0.15M NaCl, pH 8.0). 8 mg of lysozyme was added to the suspension. The suspension was incubated at 37° C. for 1 to 2 hours under shaking and then frozen. Then, 10 ml of Tris-SDS solution (1% SDS, 0.1M NaCl, 0.1M Tris, pH 9.0) was added to it under gentle shaking, followed by addition of proteinase K (Merk) at a final concentration of 0.1 mg. The mixture was incubated under shaking at 37° C. for 1 hour and then at 60°. An equal amount of phenol saturated with TE (TE: 10 mM Tris, 1 mM EDTA, pH 8.0) was added to the mixture, stirred, and centrifuged. A 2-fold excess amount of ethanol was added to the upper layer, and the DNA was recovered using a glass rod. The phenol was removed successively with 90%, 80% and 70% ethanol. Then, the DNA was dissolved in 3 ml TE buffer, and a solution of ribonuclease A (previously treated by heating at 100° C. for 15 min.) was added to it in an amount of 10 μg/ml. The mixture was incubated at 37° C. for 30 minutes under shaking, followed by addition of proteinase K. The mixture was incubated at 37° C. for 30 minutes under shaking. An equal amount of TE-saturated phenol was added to the mixture, and it was separated by centrifugation into upper and lower layers. The upper layer was subjected twice to the same procedure, followed by the same procedure of extraction with an equal amount of chloroform containing 4% isoamyl alcohol (these procedures are referred to hereinafter as phenol treatment). Then, a 2-fold excess amount of ethanol was added to the upper layer and the DNA was recovered with a glass rod whereby the chromosomal DNA was obtained.

(2) Construction of a DNA Library

10 μl plasmid pSK002 prepared by inserting into vector pUC118 a DNA fragment containing the nitrilase gene from the strain SK92 (see Reference Example) was cleaved at 37° C. for 2 hours with a mixture of 2 μl of restriction enzyme Sac I, 10 μl of the reaction buffer (10-fold conc.), and 78 μl of sterilized water, and the digest was electrophoresed on 0.7% agarose gel to separate an Sal I fragment, 1.1 kb long.

Separately, the chromosomal DNA from SK92 obtained in step (1) was digested with Eco RI, electrophoresed on agarose gel and subjected to Southern hybridization where the above 1.1 kb Sac I fragment, labeled using a DIG DNA Labeling Kit (Boehringer Mannheim), was used as the probe (Southern E. M., Mol. Bionl. 98, 503 (1975)) to detect an about 14 kb DNA fragment. A DNA fraction containing the 14 kb fragment hybridized with the probe was cut off from the agarose gel and then inserted into a separately prepared Eco RI-cleaved hybrid plasmid vector pK4 (FERM BP-3731 containing plasmid pRC004 from the genus Rhodococcus and vector pHSG299 from *E. coli* (see Japanese Laid-Open Patent Publication Nos. 64,589/1993 and 68,566/1993)).

The above pK4 fragment used as vector was prepared as follows: 10 μl of the reaction buffer (10-fold conc.), 77 βl of sterilized water and 2 μl of restriction enzyme Eco RI were added to 10 μl of vector pK4. The mixture was allowed to react at 37° C. for 2 hours, then treated with phenol, precipitated with ethanol, dried, and dissolved in 50 μl sterilized water. 1 μl of alkaline phosphatase (Takara Shuzo Co., Ltd.), 10 μl of the reaction buffer (10-fold conc.) and 39 μl of sterilized water were added to it. The mixture was allowed to react at 65° C., treated with phenol, precipitated with ethanol, dried, and dissolved in sterilized water.

As described above, 1 μl of the above DNA fraction containing the 14 kb fragment was inserted into the above Eco RI-cleaved pK4 by overnight reaction at 4° C. using a ligation kit (Takara Shuzo Co., Ltd.) to prepare a DNA library.

(3) Transformation of *E. coli* and Selection of Recombinant DNA

*E. coli* JM109 (available from Takara Shuzo Co., Ltd.) was inoculated into 1 ml of LB medium (1% Bacto-trypton extract, 0.5% Bacto-yeast extract, 0.5% NaCl) and pre-incubated at 37° C. for 5 hours. 100 μl of the culture was inoculated into 50 ml of SOB medium (2% Bacto-trypton, 0.5% Bacto-yeast extract, 10 mM NaCl, 2.5 mM KCl, 1 mM MgSO$_4$, 1 mM MgCl$_2$) and incubated at 18° C. for 20 hours. The cells were recovered by centrifugation, and the pellet was suspended in 13 ml cold TF solution (20 mM PIPES-KOH, pH 6.0, 200 mM KCl, 10 mM CaCl$_2$, 40 mM MnCl$_2$), allowed to stand at 0° C. for 10 minutes and centrifuged again. After the supernatant was removed, the *E. coli* pellet was suspended in 3.2 ml of cold TF solution, followed by addition of 0.22 ml dimethyl sulfoxide. The suspension was allowed to stand at 0° C. for 10 minutes. 10 µl of the recombinant plasmid (DNA library) prepared in step (2) was added to 200 µl of the competent cells thus prepared. The mixture was incubated at 0° C. for 30 minutes, then heat-shocked at 42° C. for 30 seconds and cooled at 0° C. for 2 minutes, followed by addition of 0.8 ml of SOC medium (2% Bacto-trypton, 0.5% Bacto-yeast extract, 20 mM glucose, 10 mM NaCl, 2.5 mM KCl, 1 mM MgSO$_4$, mM MgCl$_2$). The mixture was incubated at 37° C. for 60 minutes under shaking. The culture was plated in an amount of 200 µl per plate on LB agar medium containing 100 µg/ml ampicillin. The plate was incubated at 37° C. Selection of transformants carrying the nitrilase gene from the colonies grown on the plate was carried out by colony hybridization in the following manner. The colonies grown on the plate were transferred to a nylon membrane (Biodyne A produced by Nippon Paul) and the microorganisms were lysed. The DNA was fixed on the membrane and then hybridized with the probe (1.1 kb fragment) constructed in step (2), and the colony containing the target recombinant DNA was selected using a DIG Luminescent Detection Kit (Boehringer Mannheim).

(4) Preparation of Recombinant Plasmid

The transformant selected in step (3) was incubated at 37° C. overnight in 100 ml of LB medium, and the cells were harvested and washed with sterilized water. 5 ml of solution I (2 mM glucose, 10 mM EDTA, 25 mM Tris-HCl buffer, pH 8.0) and 25 mg lysozyme were added to the cells. It was allowed to stand at 0° C. for 30 minutes. 10 ml of solution II (1N NaOH, 5% SDS) was added thereto, and the mixture was allowed to stand at 0° C. for 5 minutes. 7.5 ml of solution III (3M sodium acetate, pH 4.8) was added thereto, and the mixture was allowed to stand at 0° C. for 30 minutes and centrifuged. 50 ml ethanol was added to the supernatant. It was centrifuged again to remove the supernatant. 5 ml of solution IV (10 mM sodium acetate, 50 mM Tris-HCl buffer, pH 8.0) and 2.5 µl of 10 mg/ml ribonuclease A were added thereto. The mixture was allowed to stand at room temperature for 20 minutes, followed by addition of 12 ml ethanol. It was centrifuged, dried, and dissolved in sterilized water.

(5) Transformation of a Microorganism of the Genus Rhodococcus, and the Nitrilase Activity of the Transformant

*Rhodococcus rhodochrous* ATCC 12674 at the logarithmic growth phase was harvested by centrifugation, washed 3 times with ice-cold sterilized water and suspended in sterilized water. 1 µg of plasmid pSK104 obtained in step (4) was mixed with 10 µl of the cell suspension, and the mixture was cooled on ice. This mixture of the DNA and the microorganism was introduced into the chamber in a electroporation apparatus CET-200 (Japan Spectroscopic Co., Ltd.), and the sample was pulsed 20 times with a density of electric field of 3.8 kV/cm and a pulse width of 1 ms. The cell suspension thus treated was placed on ice for 10 minutes and heat-shocked at 37° C. for 10 minutes. 500 µl of MYK medium (0.5% polypeptone, 0.3% Bacto-molt extract, 0.3% Bacto-yeast extract, 0.2% KH$_2$PO$_4$, 0.2% K$_2$HPO$_4$ (pH 7.0)) was added thereto. The cell suspension was then incubated at 26° C. for 3 hours under shaking. The suspension was plated on an MYK agar plate containing 75 µg/ml kanamycin and incubated at 26° C. for 3 days.

The resultant transformant of the genus Rhodococcus was inoculated into 10 ml MYK medium containing 50 µg/ml kanamycin and pre-incubated at 30° C. for 24 hours. 1 ml of the culture was added to 100 ml of GGP medium (1.5% glucose, 0.1% Bacto-yeast extract, 1.0% sodium glutamate, 0.05% KH$_2$PO$_4$, 0.05% K$_2$HPO$_4$, 0.05% MgSO$_4$ 7H$_2$O (pH 7.2)) containing 1.5% ethylene cyanohydrin (ECH) as inducer and 75 µg/ml kanamycin. The microorganism was incubated at 30° C. for 48 hours and harvested, and the pellet was suspended in 50 mM phosphate buffer, pH 7.7, and a part of the suspension was allowed to react at 30° C. for 20 minutes in 50 mM phosphate buffer, pH 7.7, containing 100 mM acrylonitrile. The reaction was stopped by addition of 1N HCl, and the amount of acrylic acid formed in the reaction solution was determined by high performance liquid chromatography (HPLC). The result indicated the formation of 8 mM acrylic acid in the transformant ATCC 12674/pSK104. It was revealed that the gene coding for the regulatory factor necessary for expression of nitrilase is present upstream or downstream of the structural gene of nitrilase.

(6) Deletion Plasmids and Nitrilase Activity

Because pSK104 was estimated to still contain a number of regions not required for expressing nitrilase, various deletion plasmids were prepared therefrom. Microorganisms transformed with the deletion plasmids were examined for their nitrilase activity (Table 1, FIG. 1).

TABLE 1

Deletion plasmids and formation of acrylic acid

| | amount of formed acrylic acid (mM) inducer (ECH) | |
|---|---|---|
| | absent | present |
| 1) pSK102 | 0 | 0 |
| 2) pSK104 | 0.77 | 8.00 |
| 3) pSK105 | 0 | 1.71 |
| 4) pSK123 | 0 | 0 |
| 5) pSK124 | 0 | 0 |
| 6) pSK106 | 1.14 | 6.38 |
| 7) pSK107 | 0 | 3.40 |
| 8) pSK125 | 0 | 0 |
| 9) pSK126 | 0 | 0 |
| 10) pSK127 | 0 | 0 |
| 11) pSK109 | 0 | 0 |
| 12) pSK108 | 0 | 8.05 |

Figure 2:
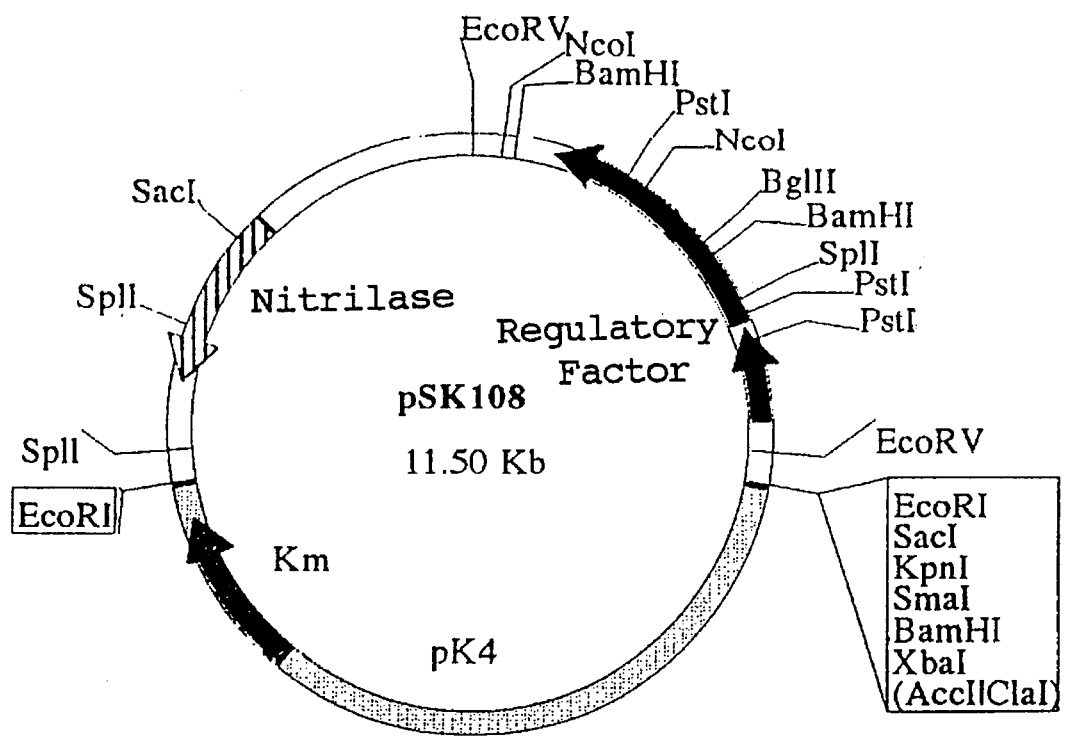
FIG. 2 shows a restriction enzyme map of recombinant plasmid pSK108.

As is evident from the table, ATCC12674/pSK108 (6.2 kb HindIIIEcoRV fragment) (FIG. 2) is of high nitrilase activity.

Additional deletion plasmids were constructed and examined for the gene coding for the regulatory factor. The result revealed that the gene is located within a far upstream region (about 3 kb BamHIEcoRV fragment) from the structural gene of nitrilase.

(7) Nucleotide Sequencing

The gene coding for the regulatory factor essential for expression of nitrilase, revealed in step (6), was sequenced using Fluorescence Sequencer ALFII (Pharmacia). The sequence analysis revealed the nucleotide sequence of SEQ ID No:5, and the presence of 2 open reading frames coding respectively for the amino acid sequences of SEQ ID Nos:1 and 2 was found. Comparison with Amino Acid Sequence Data Base NBRF (National Biomedical Research Foundation) suggested that the regulatory factor belongs to a family of two-component regulator. The nucleotide sequences of these open reading frames are shown in SEQ ID Nos:3 and 4.

Reference Example (1) Preparation of the Chromosomal DNA from the Strain SK92

The chromosomal DNA from SK92 was prepared in the same manner as in Example, step (1).

(2) Preparation of a Probe and Construction of a DNA Library

Polymerase chain reaction was carried out using 100 µl solution containing 10 µl of DNA as substrate (diluted 20-fold), 10 µl of the reaction buffer (10-fold conc.), 4 µl of 5 mM dNTP, 5 µl (500 pmol) each of 5'-AACTGCTGG-GA(AG)CACTTCCA-3' as primer #1 and 5'-GA(AG)TA(AG) TG(AG)CC(CG)AC(ACTG)GG(AG)TC-3' as primer #2 and 1 µl of Tth DNA polymerase (Toyo Boseki). The above 2 primers were prepared on the basis of amino acid sequences having high homologies with known various nitrilases. The reaction involved 50 cycles each consisting of the incubation of the sample at 93° C. for 30 seconds (denaturation step), 45° C. for 30 seconds (annealing step) and 72° C. for 2 minutes (elongation step). A 410 bp DNA fragment coding for the nitrilase from SK92 was obtained from the reaction solution. This DNA fragment was labeled as probe using a DIG DNA Labeling Kit (Boehringer Mannheim).

10 µl of the reaction buffer (10-fold conc. ), 37 µl of sterilized water and 3 µl of restriction enzyme Sal I were added to 50 µl of the chromosomal DNA from SK92. The mixture was allowed to react at 37° C. for 2 hours, then precipitated with ethanol and electrophoresed on agarose gel. A DNA fragment, about 1.1 kb, was recovered using DNA PREP (DIA-IATRON). The DNA fragment was inserted into the Sal I site of *E. coli* vector pUC118 using a ligation kit (Takara Shuzo Co., Ltd.) whereby a recombinant DNA library was prepared.

The above pUC118 fragment was prepared in the following manner. 10 µl of the reaction buffer (10-fold conc.), 77 µl of sterilized water and 2 µl of restriction enzyme Sal I were added to 10 µl of pUC118. The mixture was allowed to react at 37° C. for 2 hours, then treated with phenol, precipitated with ethanol, dried, and dissolved in 50 µl of sterilized water. 1 µl of alkaline phosphatase (Takara Shuzo Co., Ltd.), 10 µl of the reaction buffer (10-fold conc.) and 39 µl of sterilized water were added thereto. The sample solution was allowed to react at 65° C., treated with phenol, precipitated with ethanol, dried, and dissolved in sterilized water.

(3) Transformation of *E. coli* and Selection of Recombinant DNA

Competent cells of *E. coli* JM109 were prepared in the same manner as in Example, step (3). 10 µl solution (DNA library) containing the recombinant plasmid prepared in step (2) was added to 200 µl of the competent cells. The cells were allowed to stand at 0° C. for 30 minutes, then heat-shocked at 42° C. for 30 seconds and cooled at 0° C. for 2 minutes. 0.8 ml of SOC medium was added thereto, and the cells were incubated at 37° C. for 60 minutes under shaking. The culture was plated in an amount of 200 µl per plate onto LB agar medium containing 100 µg/ml ampicillin, followed by incubation at 37° C. Selection of a transformant carrying the nitrilase gene from the colonies grown on the agar medium was carried out by colony hybridization in the following manner. The transformants grown on the agar medium were transferred to a nylon membrane (Biodaine A produced by Paul Co., Ltd.) and they were lysed to fix DNA. The DNA was treated with the probe (410 bp fragment) prepared in step (2), and the colony containing the target recombinant DNA was selected using a DIG Luminescent Detection Kit (Boehringer Mannheim).

(4) Construction of Recombinant Plasmids and Preparation of a Restriction Enzyme Map The transformant selected in step (3) was treated in the same manner as in Example, step (4). The recombinant plasmid pSK002 thus obtained was cleaved with several restriction enzymes to prepare a restriction enzyme map.

(5) Production of Nitrilase by Transformed *E. coli* and Conversion of a Nitrile Into an Acid The JM109/pSK002 strain was inoculated into 1 ml of 2X YT medium (1.6% Bacto-trypton, 1.0% Bacto-yeast extract, 0.5% NaCl) containing 50 µg/ml ampicillin and incubated at 37° C. for 8 hours. ml of the culture was inoculated into 100 ml of 2X YT medium containing 50 µg/ml ampicillin and 1 mM IPTG, followed by incubation at 37° C. for 14 hours. After harvested, the microorganisms were suspended in 50 mM phosphate buffer, pH 7.7, and a part of the suspension was allowed to react at 30° C. for 20 minutes in 50 mM phosphate buffer, pH 7.7, containing 100 mM acrylonitrile. The reaction was stopped by addition of 1N HCl, and the amount of acrylic acid formed in the reaction solution was determined by HPLC. In the control test, the strain JM109 before transformation was used. The result indicates that while no acrylic acid was detected in the host JM109, the formation of 18 mM acrylic acid was found in the transformant JM109/pSK002.

(6) Introduction of the DNA Fragment Containing the Nitrilase Gene Into a Hybrid Plasmid Vector A DNA fragment (5.8 kb BglIII-HindIII fragment) containing the nitrilase structural gene and a region speculated to contain its promoter were cloned into hybrid plasmid vector pK4 whereby plasmid pSK 120 was constructed.

(7) Transformation of a Microorganism of the Genus Rhodococcus and the Nitrilase Activity of the Transformant

*Rhodococcus rhodochrous* ATCC 12674 at the logarithmic growth phase was harvested by centrifugation, washed 3 times with ice-cold sterilized water, and suspended in sterilized water. 10 µg cell suspension was mixed with 1 µg of plasmid pSK120 obtained in step (6), and the mixture was then cooled on ice. This mixture of the DNA and the microorganism was introduced into the chamber in a gene-introducing unit CET-200 (Nippon Bunko) where the sample was pulsed 20 times with a density of electric field of 3.8 kV/cm and a pulse width of 1 ms.

The cell suspension thus treated was placed on ice for 10 minutes and heat-shocked at 37° C. for 10 minutes. 500 µl of MYK medium was added to the suspension and the mixture was then incubated at 26° C. for 3 hours under shaking. The culture was plated onto MYK agar medium containing 75 µg/ml kanamycin and incubated at 26° C. for 3 days.

The thus obtained transformant of the genus Rhodococcus was inoculated into 10 ml MYK medium containing 50 µg/ml kanamycin and pre-incubated at 30° C. for 24 hours. 1 ml of the culture was added to 100 ml of GGP medium containing 75 µg/ml kanamycin. 1.5% ECH was added thereto as inducer. The transformant was incubated at 30° C. for 48 hours. After recovered, the cells were suspended in 50 mM phosphate buffer, pH 7.7, and their nitrilase activity was examined in the same manner as in step (5). No activity was found in it.

A number of references are cited herein, the disclosures of which are incorporated in their entireties by reference herein.

What is claimed is:

1. An isolated polypeptide having the sequence of SEQ ID NO:1.

2. An isolated polypeptide having the sequence of SEQ ID NO:2.

3. A regulatory system comprising (a) the polypeptide having the sequence of SEQ ID NO:1 and (b) the polypeptide having the sequence of SEQ ID NO:2.

4. An isolated nucleic acid coding for the polypeptide of claim 1.

5. The nucleic acid of claim 4 comprising the nucleotide sequence of SEQ ID NO:3.

6. An isolated nucleic acid coding for the polypeptide of claim 2.

7. The nucleic acid of claim 6 comprising the nucleotide sequence of SEQ ID NO:4.

8. An isolated nucleic acid coding for the regulatory system of claim 3.

9. The nucleic acid of claim 8 comprising the nucleotide sequence of SEQ ID NO:3 and SEQ ID NO:4.

10. The nucleic acid of claim 8 comprising the nucleotide sequence of SEQ ID NO:5.

11. A plasmid comprising (a) the nucleic acid of claim 8 and (b) a nitrilase gene and (c) nitrilase gene promoter, wherein (b) and (c) are operably linked.

12. A plasmid comprising (a) the nucleic acid of claim 10 and (b) a nitrilase gene and (c) a nitrilase gene promoter, wherein (b) and (c) are operably linked.

13. The plasmid of claim 12, wherein said plasmid is pSK104, pSK106, pSK107 or pSK108.

14. A microorganism of the genus Rhodococcus which has been transformed with the plasmid of claim 11.

15. A microorganism of the genus Rhodococcus which has been transformed with the plasmid of claim 12.

16. A method of hydrolyzing a nitrile comprising the step of contacting a nitrile with the microorganism of claim 14 wherein the nitrile is hydrolyzed.

17. The method of claim 16, comprising the additional step, prior to said contacting step, of treating said microorganism with an inducer for expression of said nitrilase gene.

18. A method of hydrolyzing a nitrile, comprising the step of contacting a nitrile with the microorganism of claim 15 wherein the nitrile is hydrolyzed.

19. The method of claim 18, comprising the additional step, prior to said contacting step, of treating said microorganism with an inducer for expression of said nitrilase gene.

* * * * *